(12) United States Patent
Cruz

(10) Patent No.: US 8,197,856 B2
(45) Date of Patent: Jun. 12, 2012

(54) KIT FOR PROMOTING HAIR GROWTH

(76) Inventor: Felix Cruz, Doral, FL (US)

( * ) Notice: Subject to any disclaimer, the term of this patent is extended or adjusted under 35 U.S.C. 154(b) by 624 days.

(21) Appl. No.: 12/191,502

(22) Filed: Aug. 14, 2008

(65) Prior Publication Data

US 2010/0040700 A1  Feb. 18, 2010

(51) Int. Cl.
*A61K 33/22* (2006.01)
(52) U.S. Cl. ....... 424/659; 424/490; 424/61; 424/78.35; 424/489; 424/672; 424/70.21; 424/404; 514/725
(58) Field of Classification Search .................. 424/490, 424/61, 78.35, 489, 672, 404, 70.21; 514/725
See application file for complete search history.

(56) References Cited

U.S. PATENT DOCUMENTS

2003/0072806 A1* 4/2003 Marrodan ...................... 424/489
2005/0095215 A1* 5/2005 Popp .......................... 424/70.21

* cited by examiner

*Primary Examiner* — James J Seidleck
*Assistant Examiner* — Anna Falkowitz
(74) *Attorney, Agent, or Firm* — Ruben Alcoba, Esq.

(57) ABSTRACT

A kit for promoting hair growth on areas of the scalp that has been affected by fungal infections. The kit reduces the loss of hair, gradually destroys the cause of the loss of hair, and eventually restores the normal hair growth in the areas of the scalp affected by the fungi. The kit is comprised of a first powdered mixture and three liquid compositions. The elements of the kit are applied to the scalp of an individual experiencing hair loss due to fungi.

6 Claims, 2 Drawing Sheets

KIT FOR PROMOTING HAIR GROWTH

BACKGROUND

Figure 1:

The present invention is related to a kit that will promote hair growth in areas where hair growth has been diminished due to fungi.

It is well known that in order to produce healthy and strong hair that a healthy scalp environment is needed. There are certain scalp skin disorders that will affect the growth of hair that might be able to be controlled.

Seborrheic dermatitis might be a scalp condition that affects the normal growth of hair. The symptoms of seborreheic dermatitis are scaly skin, itchy dandruff and red skin. Many people who suffer from this condition have abnormal sebum (oil) production. This means that they produce more oil than necessary for natural skin lubrication. Some people who have abnormal sebum production might have a yeast or fungus called malassezia growing in the sebum of their scalp along with other bacteria.

Tinea capitis is another fungal infection that affects hair growth on the scalp. Tinea capitis usually causes patches of hair to fall from the scalp. The fungus propagates on the hair fibers of the affected area. The hairs of the affected area become brittle and fall off easily, thereby leaving bald patches of skin on the scalp of people affected by the fungus.

There are at least four types of fungi that can cause ring worm of the scalp, tinea capitis. Some of the fungi are *microsporum audouini, trichophyton tonsurans, trichophyton schoenleinii,* and *trichophyton megninii*. The fungi are opportunistic and usually enter the scalp through a cut or a scrape. Once in the scalp, the fungi multiply and spread out in circles. The fungi locate themselves around the growing hair follicles, which in turn cause the follicles to become weaker and eventually fall out.

At the present time, tinea capitis is treated using antibiotics. Dandruff shampoos may be used to treat seborrheic dermatitis, yet they are not strong enough to cure tinea capitis. Tinea capitis usually can be treated within a period of 7 months, yet in some extreme cases, the period may be much longer.

An object of the present invention is to provide people who suffer from the loss of hair from seborrheic dermatitis or tinea capitis with a kit, that when used daily, will reduce the loss of hair, gradually destroy the cause of the loss of hair, and eventually restore the normal hair growth in the areas of the scalp affected by the fungi.

SUMMARY

The present invention is directed to a kit for promoting hair growth on areas of the scalp that have been affected by fungal infections. The kit reduces the loss of hair, gradually destroys the cause of the loss of hair, and eventually restores the normal hair growth in the areas of the scalp affected by the fungi. The kit comprises of a first powdered mixture and three liquid compositions. The elements of the kit are applied to the scalp of an individual experiencing hair loss due to fungi.

The powdered mixture is 99 percent boric acid and 1 percent tolnaftate. The mixture is applied on to the affected areas of the scalp of the user.

The first liquid compositions of the kit is composed of a hydrochloric acid solution, an isopropyl solution, an all purpose cleaner, a terbinafine liquid, a mineral oil, and a cleansing agent. The first liquid composition is applied to the scalp after the powdered mixture has been applied to the affected areas and is massaged onto the scalp. The first liquid composition helps dilute the first powdered mixture. The combination of the first powdered mixture and the first liquid mixture are left on the scalp of the user for at least 3 hours.

The second liquid composition of the kit is composed of an all purpose cleaner, a 50 percent isopropyl solution, and a hydrocloric acid solution. The second liquid composition is applied to the scalp after applying the powdered mixture and the first liquid composition 2 times to the scalp, without washing off the powdered mixture and the first liquid composition. The second liquid composition is applied on the affected area while brushing the scalp with a brush or comb until any dried skin is removed.

The third liquid composition of the kit composed of a cleansing agent, an all purpose cleaner, a hydrocloric acid solution, and a mineral oil. The third liquid composition is applied to the scalp on the second day after the initial use of the kit and is used to wash off all of powdered mixture, first liquid composition, and the second liquid composition used on the scalp of the affected area. The third liquid composition is also used to moisturize the affected area.

The kit is used in two day cycles for a period of at least five months. The inventor recommends life style changes to the users of his kit, more specifically he recommends that users eat nutritious foods during and after the use of his kit in order to promote healthy hair growth.

DRAWINGS

Figure 2:

The foregoing aspects and many of the attendant advantages of this invention will become more readily appreciated as the same become better understood by reference to the following detailed description, when taken in conjunction with the accompanying drawings, wherein:

FIG. 1 shows a picture of the scalp of the inventor prior to using the kit of the present invention; and FIG. 2 shows a picture of the scalp of the inventor six months after he first used the kit.

DESCRIPTION

The present invention is a kit for promoting hair growth on areas of the scalp that have been affected by fungal infections, comprises of a powdered mixture, a first liquid composition, a second liquid composition, and a third liquid composition.

The powdered mixture composition is 99 percent boric acid and 1 percent tolnaftate by weight.

The first liquid composition is composed of a hydrocloric acid solution having a volume from at least 20 to at most 30 percent of the first liquid composition, a 50 percent isopropyl solution having a volume from at least 25 to at most 35 percent of the first liquid composition, an all purpose cleaner having a volume from at least 35 to at most 45 percent of the first liquid composition, a terbinafine liquid having a volume from at least 1 to at most 5 percent of the first liquid composition, a mineral oil having a volume from at least 1 to at most 5 percent of the first liquid composition, and a cleansing agent consisting of soaps or detergents used for washing hair, shampoo, having a volume from at least 5 to at most 10 percent of the first liquid composition.

The second liquid compisition is composed of an all purpose cleaner having a volume from at least 45 to at most 50 percent of the second liquid composition, a 50 percent isopropyl solution having a volume from at least 45 to at most 50 percent of the second liquid composition, and a hydrocloric acid solution having a volume from at least 1 to at most 3 percent of the second liquid composition.

The third liquid composition is composed of a cleansing agent consisting of soaps or detergents used for washing hair, shampoo, having a volume from at least 85 to at most 90 percent of the third liquid composition, an all purpose cleaner having a volume from at least 5 to at most 10 percent of the third liquid composition, a hydrocloric acid solution having a volume from at least 1 to at most 3 percent of the second liquid composition, and a mineral oil having a volume from at least 0.5 to at most 3 percent of the third liquid composition.

The hydrochloric acid solution used in all of the liquid compositions has the molecular weight of 36.46.

In one embodiment of the present invention the all purpose cleaner used in the liquid compositions 1-3 is by weight from about 0.5 to about 1.5 surfactants and at least 95 percent water.

In another embodiment of the present invention the all purpose cleaner used in the liquid compositions 1-3 is composed of ionic and nonionic surfactants, alcohol, perfume, preservative, water and color.

The kit is used in two day cycles. The kit is used by first, providing the kit. On the first day of treatment, applying the powdered mixture of the kit to affected areas of the scalp. Next, applying the first liquid composition to the powdered mixture and then massaging the first liquid and mixture composition on the scalp of the affected area, then leaving the first liquid and mixture composition on the scalp for a period of at least three hours. Then, reapplying the powdered mixture and the first liquid composition in the same manner recited above and leaving the first liquid and mixture composition on the affected areas for at least three hours. Next, applying the second liquid composition on the skin while brushing the scalp with a brush or comb until any dried skin is removed. On the second date of treatment, reapplying the powdered mixture, the first liquid composition, and the second liquid compositions in the same manner in which they were applied above and at the same time intervals. Then, applying the third liquid composition to the affected areas, thereby washing the powdered mixture and liquid compositions from the scalp of the affected area. And, lastly lightly reapplying the third liquid composition to the affected areas and leaving the third liquid composition on the affected areas.

The kit is to be used daily for a period of at least 5 months.

The inventor of the present invention suffers from what he believes is hair loss caused by seborrheic dermatitis. He has used the kit for a period of at least six months and believes that he has experienced at least a 60 percent increase of hair growth on the areas affected by seborrheic dermatitis.

An advantage of the present invention is that it provides people who suffer from the loss of hair from seborrheic dermatitis or tinea capitis with a kit that will reduce the loss of hair, gradually destroy the cause of the loss of hair, and eventually restore the normal growth of hair in the areas of the scalp affected by the fungi.

The invention claimed is:

1. A kit for promoting hair growth on areas of the scalp that have been affected by fungal infections, comprising:
a powdered mixture composition of 99 percent boric acid and 1 percent tolnaftate by weight;
a first liquid composition composed of:
a hydrochloric acid solution having a volume from at least 20 to at most 30 percent of the first liquid composition;
a 50 percent isopropyl solution having a volume from at least 25 to at most 35 percent of the first liquid composition;
an all purpose cleaner having a volume from at least 35 to at most 45 percent of the first liquid composition;
a terbinafine liquid having a volume from at least 1 to at most 5 percent of the first liquid composition;
a mineral oil having a volume from at least 1 to at most 5 percent of the first liquid composition; and
a cleansing agent consisting of soaps or detergents used for washing hair, shampoo, having a volume from at least 5 to at most 10 percent of the first liquid composition;
a second liquid compisition composed of:
an all purpose cleaner having a volume from at least 45 to at most 50 percent of the second liquid composition;
a 50 percent isopropyl solution having a volume from at least 45 to at most 50 percent of the second liquid composition; and
a hydrocloric acid solution having a volume from at least 1 to at most 3 percent of the second liquid composition; and
a third liquid composition composed of:
a cleansing agent consisting of soaps or detergents used for washing hair, shampoo, having a volume from at least 85 to at most 90 percent of the third liquid composition;
an all purpose cleaner having a volume from at least 5 to at most 10 percent of the third liquid composition;
a hydrocloric acid solution having a volume from at least 1 to at most 3 percent of the second liquid composition; and
a mineral oil having a volume from at least 0.5 to at most 3 percent of the third liquid composition.

2. The kit for promoting hair growth on areas of the scalp that have been affected by fungal infections of claim 1, wherein the hydrochloric acid solutions used in the liquid compositions 1-3 have a molecular weight of 36.46.

3. The kit for promoting hair growth on areas of the scalp that have been affected by fungal infections of claim 2, wherein the all purpose cleaner used in the liquid compositions 1-3 is by weight from about 0.5 to about 1.5 surfactants and at least 95 percent water.

4. The kit for promoting hair growth on areas of the scalp that have been affected by fungal infections of claim 2, wherein the all purpose cleaner used in the liquid compositions 1-3 is composed of ionic and nonionic surfactants, alcohol, perfume, preservative, water and color.

5. A method of using the kit of claim 1 to promote hair growth on areas of the scalp that have been affected by fungal infections, comprising the steps of:
a. first, providing the kit of claim 1;
on the first day of treatment, applying the powdered mixture of the kit to affected areas of the scalp;
b. next, applying the first liquid composition to the powdered mixture and then massaging the first liquid and mixture composition on the scalp of the affected area, then leaving the first liquid and mixture composition on the scalp for a period of at least three hours;

c. then, reapplying the powdered mixture and the first liquid composition in the same manner recited above and leaving the first liquid and mixture composition on the affected areas for at least three hours;

d. next, applying the second liquid composition on the skin while brushing the scalp with a brush or comb until any dried skin is removed;

the next day, reapplying the powdered mixture, the first liquid composition, and the second liquid compositions in the same manner in which they were applied above and at the same time intervals;

e. then, applying the third liquid composition to the affected areas, thereby washing the powdered mixture and liquid compositions from the scalp of the affected area; and f. lastly, lightly reapplying the third liquid composition to the affected areas and leaving the third liquid composition on the affected areas.

6. The method of using the kit of the claim 4, further comprising the step of repeating steps a-f daily for a period of at least 5 months.

* * * * *